United States Patent [19]

Epp et al.

[11] Patent Number: 4,904,591
[45] Date of Patent: Feb. 27, 1990

[54] CARBOMYCIN RESISTANCE-CONFERRING GENE, DESIGNATED CARA, FOR USE IN STREPTOMYCES AND OTHER ORGANISMS

[75] Inventors: Janet K. Epp, Indianapolis; Brigitte E. Schoner, Zionsville, both of Ind.

[73] Assignee: Eli Lilly and Company, Indianapolis, Ind.

[21] Appl. No.: 901,240

[22] Filed: Aug. 28, 1986

[51] Int. Cl.$^4$ ............... C12R 1/465; C07H 15/12; C12N 15/00; C12N 1/20; C12N 1/00; C12P 21/00

[52] U.S. Cl. .................. 435/172.3; 435/886; 435/252.35; 435/172.1; 435/253.5; 435/320; 536/27; 935/14; 935/19; 935/27; 935/60

[58] Field of Search ............ 435/76, 91, 172.1, 172.3, 435/253, 255, 256, 320, 886; 536/27; 935/19, 23, 27, 38, 55, 60, 14

[56] References Cited

U.S. PATENT DOCUMENTS 2,902,412  9/1959  Pagano et al. .................. 435/76

OTHER PUBLICATIONS

Benveniste and Davies, 1973, Proc. Natl. Acad. Sci. USA 70(8): 2276–2280.
Thompson et al., 1980, Nature 286:525–527.
Fujisawa and Weisblum, 1981, J. Bacteriol. 146(2):621–631.
Thompson et al., 1982, J. Bacteriol. 151(2):668–677; 678–685.
Murakami et al., 1983, J. Antibiotics 37(12):1305–1311.
Tohyama et al., 1984, J. Antibiotics 37(12):1736–1737.
Thompson et al., 1982, Gene, 20:51–62.
Nakano et al., 1984, J. Bacteriol. 157(1):79–83.
Bibb et al., 1985, Mol. Gen. Genet. 199:26–36.
Ohnuki et al., 1985, J. Bacteriol. 161(3):1010–1016.
Distler et al., 1985, FEMS Microbiology Letters 30:151–154.
Vara et al., 1985, Gene 33:197–206.
Birmingham et al., 1984, Abstracts of the ASM Conference on Genetics and Molecular Biology of Industrial Microorganisms, Bloomington, IN, Abstract No. 220.
Uchiyama and Weisblum, 1985, Gene 38:103–110.

Primary Examiner—Thomas G. Wiseman
Assistant Examiner—Joan Ellis
Attorney, Agent, or Firm—Douglas K. Norman; Leroy Whitaker

[57] ABSTRACT

The carA gene is a novel carbomycin resistance-conferring gene isolated from Streptomyces thermotolerans and used to construct a number of cloning vectors for use in Streptomyces and related organisms. One such cloning vector, plasmid pOJ158, can be obtained in S. griseofuscus C581 under the accession number NRRL 18089. S. lividans and S. griseofuscus are the preferred hosts when the carA gene is used to select carbomycin-resistant Streptomyces transformants.

19 Claims, 3 Drawing Sheets pOJ158

Figure 1
Restriction Site and Function Map of Plasmid pOJ158 pOJ158

Figure 2
Restriction Site and Function Map of Plasmid pOJ197 pOJ197

Figure 3
Restriction Site and Function Map of Plasmid pOJ160 pOJ160

CARBOMYCIN RESISTANCE-CONFERRING GENE, DESIGNATED CARA, FOR USE IN STREPTOMYCES AND OTHER ORGANISMS

SUMMARY OF THE INVENTION

The present invention comprises a novel carbomycin resistance-conferring gene, designated carA, a method for using the carA gene, recombinant DNA cloning vectors that comprise the novel gene, and transformants containing the carbomycin resistance-conferring vectors. *Streptomyces thermotolerans* (ATCC 11416) produces carbomycin, a macrolide antibiotic consisting of a 16-member cyclic lactone and two sugar residues. The antibiotic activity of carbomycin, like that of other macrolides, is due to inhibition of protein synthesis by a mechanism that involves the binding of carbomycin to the ribosome.

The present invention provides carbomycin resistance-conferring cloning vectors for use in Streptomyces and other host cells. The development and exploitation of recombinant DNA technology in Streptomyces depends upon the availability of selectable genetic markers on suitable cloning vectors. This development has been somewhat retarded by the low number of selectable markers presently available for use in Streptomyces. The present invention is useful and especially important in that it expands the number of selectable markers suitable for such use.

The vectors of the present invention are particularly useful, because the vectors are small, versatile, and can be transformed and selected in a variety of carbomycin-sensitive Streptomyces cells. Streptomyces provides over half of the clinically important antibiotics and thus is a commercially significant group. The present invention provides new and useful cloning systems and vectors for this industrially important group and allows for the cloning of genes both for increasing the yields of known antibiotics and also for producing new antibiotics and antibiotic derivatives.

The present invention further provides vectors that enable identification of Streptomyces transformants. After the addition of non-selectable DNA to a vector of the present invention, the modified vector can be transformed into Streptomyces and transformants identified by their carbomycin-resistant phenotype. Because transformation is a relatively low frequency event, such a functional test is a practical necessity for determining which cell(s), of among the millions of cells, has acquired the transforming DNA.

For purposes of the present invention, as disclosed and claimed herein, the following terms are defined below.

ApR—the ampicillin-resistant phenotype or gene conferring same.
carA—a carbomycin resistance-conferring gene of type A.
carB—a carbomycin resistance-conferring gene of type B.
mel—the tyrosinase gene.
Phasmid—a recombinant DNA vector that may act as a phage or as a plasmid.
Recombinant DNA Cloning Vector—any autonomously replicating or integrating agent, including, but not limited to, plasmids, comprising a DNA molecule to which one or more additional DNA segments can be or have been added.
Restriction Fragment—any linear DNA molecule generated by the action of one or more restriction enzymes.
Sensitive Host Cell—a host cell that cannot grow in the presence of a given antibiotic without a DNA segment that provides resistance thereto.
TcR—the tetracycline-resistant phenotype or gene conferring same.
Transformant—a recipient host cell that has undergone transformation.
Transformation—the introduction of DNA into a recipient host cell that changes the genotype and results in a change in the recipient cell.
tsrR—the thiostrepton-resistant phenotype or gene conferring same.

BRIEF DESCRIPTION OF THE FIGURES

The figures described below are drawn to scale; however, observed restriction fragment size may vary somewhat from calculated size based on map distances. For some restriction enzymes, such as SauIIIAl, only the significant cut sites are shown.

DETAILED DESCRIPTION OF THE INVENTION

Figure 1:
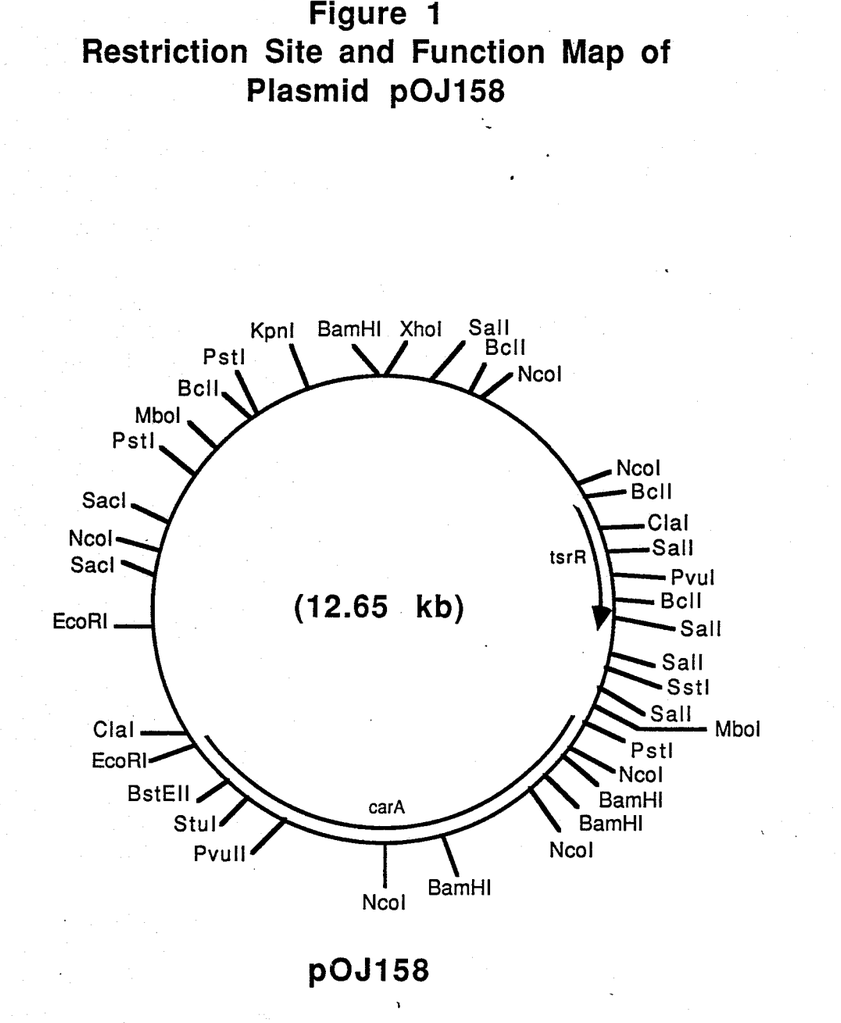
FIG. 1 is a restriction site and function map of plasmid pOJ158.

The present invention concerns a novel carbomycin resistance-conferring gene, designated carA, that is useful as a genetic marker in many organisms. The carA gene is useful in a method for selecting a recombinant DNA-containing host cell that comprises transforming a carbomycin-sensitive host cell with a recombinant DNA vector that codes for expression of the carA gene product and culturing the transformed cell under conditions suitable for selection of carbomycin-resistant transformants. The carA gene can be isolated from plasmid pOJ158 on an ~4 kb PstI-EcoRI restriction fragment; plasmid pOJ158 can be isolated from *Streptomyces griseofuscus* C581/pOJ158, a strain deposited and made part of the permanent culture collection of the Agricultural Research Service, Northern Regional Research Center (NRRL), Peoria, Ill. 61604, under the accession number NRRL 18089. A restriction site and function map of plasmid pOJ158 is presented in FIG. 1 of the accompanying drawings. Plasmid pOJ158 can be isolated from *S. griseofuscus* C581/pOJ158 in substantial accordance with the procedure described in Example 1.

Figure 2:
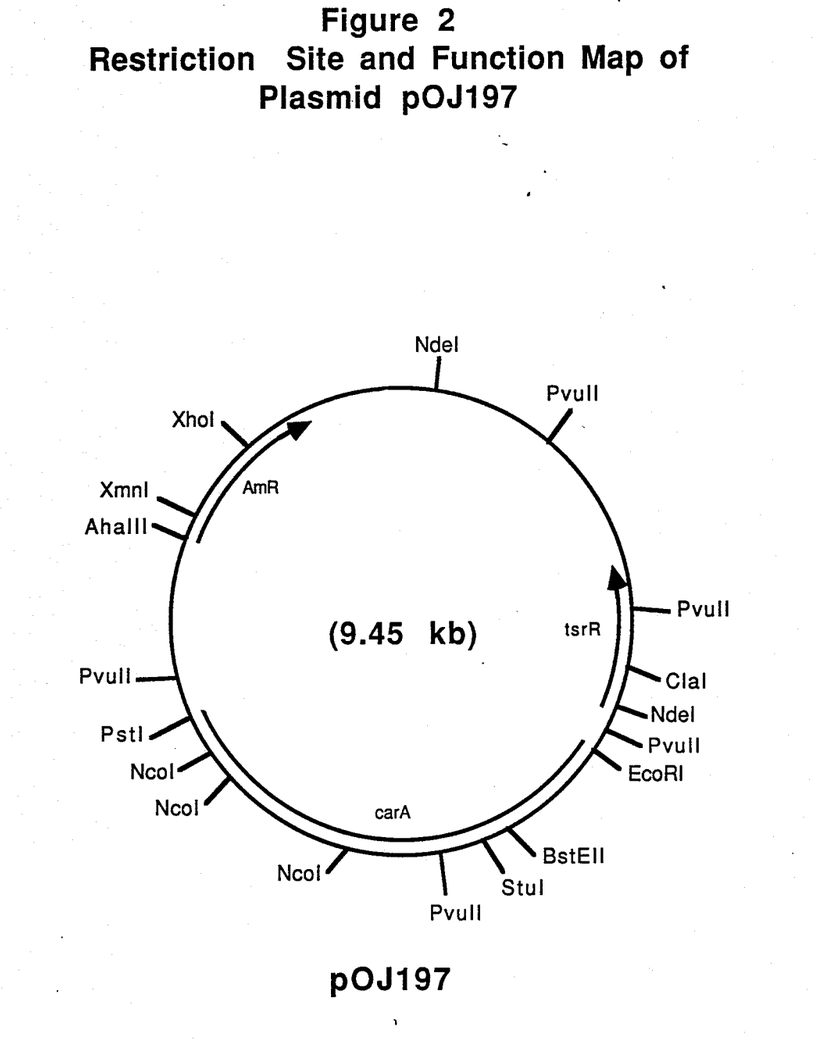
FIG. 2 is a restriction site and function map of plasmid pOJ197.
Figure 3:
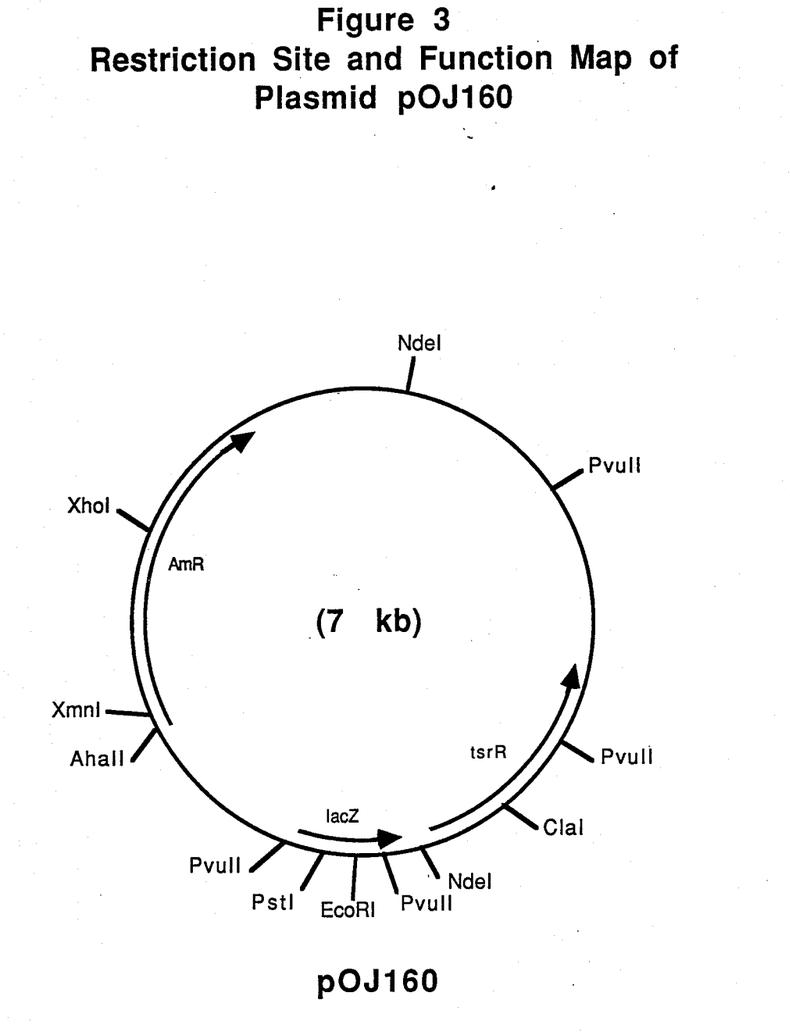
FIG. 3 is a restriction site and function map of plasmid pOJ160.

Plasmid pOJ158 serves as useful starting material for the construction of other vectors that confer carA-mediated carbomycin resistance. For example, the ~4 kb PstI-EcoRI, carbomycin resistance-conferring restriction fragment of plasmid pOJ158 was isolated and inserted into EcoRI-PstI-digested plasmid pOJ160 (NRRL B-18088) to yield plasmid pOJ197. The construction protocol for plasmid pOJ197 is given in Example 2; a restriction site and function map of plasmid pOJ197 is presented in FIG. 2 of the accompanying drawings.

The carA gene was isolated from a carbomycin-producing strain of *Streptomyces thermotolerans* (ATCC 11416). Thus, genomic DNA of *S. thermotolerans* was partially digested with restriction enzyme MboI, and the resulting DNA was inserted into BglII-digested plasmid pIJ702 (ATCC 39155, Katz et al., 1983, J. Gen. Microbiol. 129:2703) to yield a number of carA-containing plasmids, including plasmid pOJ158. Because the carA gene was isolated from *S. thermotolerans*, the carA gene functions in *S. thermotolerans*, but the carA gene with its natural promoter also functions in other organisms.

The vectors of the present invention have been used to transform *Streptomyces lividans* TK23 (NRRL 15826) and *Streptomyces griseofuscus* C581 (ATCC 23916) to carbomycin resistance, as described in Example 3. Thus, the carA gene can be used to transform a variety of carbomycin-sensitive Streptomyces strains to carbomycin resistance. In organisms naturally sensitive to macrolide antibiotics, including carbomycin, the carA gene can be used as a genetic marker. In organisms that produce one or more macrolide antibiotics yet are sensitive to low levels of macrolide antibiotic, the vectors of the present invention can be used to increase or augment the organism's natural resistance. The following Tables present a representative sampling of various antibiotic-producing organisms in which the carA gene can be used.

TABLE I
Aminocyclitol Antibiotic-Producing Organisms

| Organism | Antibiotic |
|---|---|
| Bacillus | |
| various species | various aminocyclitols |
| Micromonospora | |
| various species | gentamycins |
| Saccharopolyspora | |
| various species | various aminocyclitols |
| Streptomyces | |
| albogriseolus | neomycins |
| albus var. metamycinus | metamycin |
| aquacanus | N—methyl hygromycin B |
| atrofaciens | hygromycins |
| bikiniensis | streptomycin |
| bluensis var. bluensis | bluensomycin |
| canus | ribosyl paromamine |
| catenulae | catenulin |
| chrestomyceticus | aminosidine |
| crystallinus | hygromycin A |
| erythrochromogenes var. narutoensis | streptomycin |
| eurocidicus | A16316-C |
| fradiae | hybrimycins and neomycins |
| fradiae var. italicus | aminosidine |
| galbus | streptomycin |
| griseus | streptomycin |
| griseoflavus | MA 1267 |
| hofuensis | seldomycin complex |
| hygroscopicus | hygromycins, leucanicidin, and hygrolidin |
| hygroscopicus forma glebosus | glebomycin |
| hygroscopicus var. limoneus | validamycins |
| hygroscopicus var. sagamiensis | spectinomycin |
| kanamyceticus | kanamycin A and B |
| kasugaensis | kasugamycins |
| kasugaspinus | kasugamycins |
| lavendulae | neomycin |
| lividus | lividomycins |
| mashuensis | streptomycin |
| microsporeus | SF-767 |
| netropsis | LL-AM31 |
| noboritoensis | hygromycins |
| olivaceus | streptomycin |
| olivoreticuli var. cellulophilus | destomycin A |
| poolensis | streptomycin |
| rameus | streptomycin |
| ribosidificus | SF733 |

TABLE I-continued
Aminocyclitol Antibiotic-Producing Organisms

| Organism | Antibiotic |
|---|---|
| rimofaciens | destomycin A |
| rimosus forma paromomycinus | paromomycins and catenulin |
| spectabilis | spectinomycin |
| tenebrarius | tobramycin and apramycin |
| Streptoverticillium | |
| flavopersicus | spectinomycin |

TABLE II
Ansamycin Antibiotic-Producing Organisms

| Organism | Antibiotic |
|---|---|
| Micromonospora | |
| various species | various ansamycins |
| Nocardia | |
| mediterranei | rifamycin |
| Streptomyces | |
| collinus | ansatrienes and napthomycins |
| diastochromogenes | ansatrienes and napthomycins |
| galbus subsp. griseosporeus | napthomycin B |
| hygroscopicus | herbimycin |
| hygroscopicus var. geldanus var. nova | geldamycin |
| nigellus | 21-hydroxy-25-demethyl 25-methylthioproto-streptovaricin |
| rishiriensis | mycotrienes |
| sp. E/784 | actamycin and mycotrienes |
| sp. E88 | mycotrienes |
| spectabilis | streptovaricins |
| tolypophorous | tolypomycin |

TABLE III
Anthracycline and Quinone Antibiotic-Producing Organisms

| Organism | Antibiotic |
|---|---|
| Streptomyces | |
| caespitosus | mitomycins A, B, and C |
| coelicolor | actinorhodin |
| coeruleorubidicus | daunomycin |
| cyaneus | ditrisarubicin |
| flavogriseus | cyanocycline A |
| galilaeus | aclacinomycin A, auramycins, and sulfurmycins |
| lusitanus | napthyridinomycin |
| peuceticus | daunomycin and adriamycin |
| violochromogenes | arugomycin |

TABLE IV
β-Lactam Antibiotic-Producing Organisms

| Organism | Antibiotic |
|---|---|
| Agrobacterium | various β-lactams |
| Cephalosporium | |
| acremonium | penicillins and cephalosporins |
| Chromobacterium | various β-lactams |
| Gluconobacter | various β-lactams |
| Nocardia | |
| lactamadurans | cephamycin C |
| uniformis | nocardicin |
| Penicillium | |
| chrysogenum | various penicillins and other β-lactams |
| Serratia | various β-lactams |
| Streptomyces | |

TABLE IV-continued
β-Lactam Antibiotic-Producing Organisms

| Organism | Antibiotic |
|---|---|
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, penicillins cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxycephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| rochei | cephamycin A and B |
| sioyaensis | MM 4550 and MM 13902 |
| sp. OA-6129 | OA-6129A |
| sp. KC-6643 | carpetimycin A |
| viridochromogenes | cephamycin A and B |
| wadayamensis | WS-3442-D |

TABLE V
Macrolide, Lincosamide, and Streptogramin Antibiotic-Producing Organisms

| Organism | Antibiotic |
|---|---|
| Micromonospora | |
| rosaria | rosaramicin |
| Streptomyces | |
| albireticuli | carbomycin |
| albogriseolus | mikonomycin |
| albus | albomycetin |
| albus var. coilmyceticus | coleimycin |
| ambofaciens | spiramycin and foromacidin D |
| antibioticus | oleandomycin |
| avermitilis | avermectins |
| bikiniensis | chalcomycin |
| bruneogriseus | albocycline |
| caelestis | M188 and celesticetin |
| cinerochromogenes | cineromycin B |
| cirratus | cirramycin |
| deltae | deltamycins |
| djakartensis | niddamycin |
| erythreus | erythromycins |
| eurocidicus | methymycin |
| eurythermus | angolamycin |
| fasciculus | amaromycin |
| felleus | argomycin and picromycin |
| fimbriatus | amaromycin |
| flavochromogenes | amaromycin and shincomycins |
| fradiae | tylosin |
| fungicidicus | NA-181 |
| fungicidicus var. espinomyceticus | espinomycins |
| furdicidicus | mydecamycin |
| goshikiensis | bandamycin |
| griseofaciens | PA133A and B |
| griseoflavus | acumycin |
| griseofuscus | bundlin |

TABLE V-continued
Macrolide, Lincosamide, and Streptogramin Antibiotic-Producing Organisms

| Organism | Antibiotic |
|---|---|
| griseolus | griseomycin |
| griseospiralis | relomycin |
| griseus | borrelidin |
| griseus ssp. sulphurus | bafilomycins |
| halstedi | carbomycin and leucanicidin |
| hygroscopicus | tylosin |
| hygroscopicus subsp. aureolacrimosus | milbemycins |
| kitastoensis | leucomycin $A_3$ and josamycin |
| lavendulae | aldgamycin |
| lincolnensis | lincomycin |
| loidensis | vernamycin A and B |
| macrosporeus | carbomycin |
| maizeus | ingramycin |
| mycarofaciens | acetyl-leukomycin, and espinomycin |
| narbonensis | josamycin and narbomycin |
| narbonensis var. josamyceticus | leucomycin $A_3$ and josamycin |
| olivochromogenes | oleandomycin |
| platensis | platenomycin |
| rimosus | tylosin and neutramycin |
| rochei | lankacidin and borrelidin |
| rochei var. volubilis | T2636 |
| roseochromogenes | albocycline |
| roseocitreus | albocycline |
| spinichromogenes var. suragaoensis | kujimycins |
| tendae | carbomycin |
| thermotolerans | carbomycin |
| venezuelae | methymycins |
| violaceoniger | lankacidins and lankamycin |

TABLE VI
Miscellaneous Antibiotic-Producing Streptomyces

| Antibiotic Type | Streptomyces Species | Antibiotic |
|---|---|---|
| amino acid analogues | sp. | cycloserine |
| cyclopentane ring-containing | coelicolor | methylenomycin A |
| | erythrochromogenes | sarkomycin |
| | Kasugaensis | aureothricin and thiolutin |
| | violaceoruber | methylenomycin A |
| nitro-containing | venezuelae | chloramphenicol |
| polyenes | griseus | candicidin |
| | nodosus | amphotericin B |
| | noursei | nystatin |
| tetracyclines | aureofaciens | tetracycline, chlor-tetracycline, demethyltetracycline, and demethylchlortetracycline |
| | rimosus | oxytetracycline |

TABLE VII
Nucleoside Antibiotic-Producing Organisms

| Organism | Antibiotic |
|---|---|
| Corynebacterium | |
| michiganese pv. rathayi | tunicamycin analogues |
| Nocardia | |
| candidus | pyrazofurin |
| Streptomyces | |
| antibioticus | ara-A |
| chartreusis | tunicamycin |
| griseoflavus var. | streptoviridans |

TABLE VII-continued

| Nucleoside Antibiotic-Producing Organisms | |
|---|---|
| Organism | Antibiotic |
| *thuringiensis* | |
| *griseolus* | sinefungin |
| *lysosuperificus* | tunicamycin |

TABLE VIII

| Peptide Antibiotic-Producing Organisms | |
|---|---|
| Organism | Antibiotic |
| Actinoplanes | |
| *missouriensis* | actaplanin |
| *teichomyceticus* | teicoplanin |
| Bacillus | |
| various species | bacitracin, polymixin, and colistin |
| Nocardia | |
| *candidus* | A-35512 and avoparcin |
| *lurida* | ristocetin |
| *orientalis* | vancomycin |
| Streptomyces | |
| *antibioticus* | actinomycin |
| *aureus* | thiostrepton |
| *canus* | amphomycin |
| *eburosporeus* | LL-AM374 |
| *haranomachiensis* | vancomycin |
| *pristinaespiralis* | pristinamycin |
| *roseosporus* | lipopeptides, such as A21978C |
| *toyocaensis* | A47934 |
| *virginiae* | A41030 |

TABLE IX

| Polyether Antibiotic-Producing Organism | |
|---|---|
| Organism | Antibiotic |
| Actinomadura | |
| various species | various polyethers |
| *oligosporus* | A80190 |
| Dactylosporangium | |
| various species | various polyethers |
| Nocardia | |
| various species | various polyethers |
| Streptomyces | |
| *albus* | A204, A28695A and B, and salinomycin |
| *aureofaciens* | narasin |
| *bobili* | A80438 |
| *cacaoi* var. *asoensis* | lysocellin |
| *chartreusis* | A23187 |
| *cinnamonensis* | monensin |
| *conglobatus* | ionomycin |
| *eurocidicus* var. *asterocidicus* | laidlomycin |
| *flaveolus* | CP38936 |
| *gallinarius* | RP 30504 |
| *griseus* | grisorixin |
| *hygroscopicus* | A218, emericid, DE3936, A120A, A28695A and B, etheromycin, and dianemycin |
| *lasaliensis* | lasalocid |
| *longwoodensis* | lysocellin |
| *mutabilis* | S-11743a |
| *pactum* | A80438 |
| *ribosidificus* | lonomycin |
| *violaceoniger* | nigericin |
| Streptoverticillium | |
| various species | various polyethers |

As the carA gene was isolated from *Streptomyces thermotolerans*, the carA gene should function in most Streptomyces species. Yet even if the intact carA gene failed to express in a given organism, such as *E. coli*, because, for example, the Streptomyces promoter failed to function in that organism, the carA protein-coding sequence of the present invention could be ligated to a DNA containing an appropriate promoter and ribosome-binding site to achieve expression of the carA gene. Thus, the carA protein-coding sequence is useful in all carbomycin-sensitive, prokaryotic host cells.

Plasmid pOJ158 contains the complete carA gene: (1) a promoter that directs transcription of the protein-coding sequence; (2) a sequence that, when transcribed into mRNA, directs translation of the transcript; and (3) a protein-coding sequence. Each of these elements is independently useful and can, through the techniques of recombinant DNA technology, be used to form recombinant genes of great variety. The DNA sequence of the carA gene can be obtained using standard techniques (Maxam and Gilbert, 1980, Methods in Enzymology 65:449–560 and Sanger et al., Proc. Natl. Acad. Sci. 74:5463–5467) and will reveal the location of the carA coding sequence. Such information allows one to position other promoters, for example, the trp, lpp, and lac promoters of *E. coli* and the veg promoter of Bacillus, in reading phase with the carA coding sequence. By choosing the proper promoter, one can construct vectors that drive expression of the carA gene product in any given host cell. The promoter of the carA gene is useful in its own right. The promoter and other regulatory elements the carA gene can be linked to the coding sequence of a non-carbomycin antibiotic biosynthetic gene to prepare a hybrid antibiotic pathway gene that functions in another Streptomyces species to yield a hybrid antibiotic. Thus, the individual elements of the gene on the plasmids described herein comprise important components of the present invention.

Those skilled in the art will recognize that the carA sequence deposited under accession number NRRL 18089 can be used to prepare synthetic or natural DNA probes for use in obtaining other macrolide, lincosamide, and streptogramin (MLS) resistance-conferring genes. In addition, due to the diversity of *Streptomyces thermotolerans* strains both in nature and also in the laboratory, there will be a variety of allelic variants of the carA gene that can be readily isolated by using the carA gene as a probe to identify homologous DNA. These allelic variants, which encode gene products with an amino acid residue sequence that differs from that of the carA gene product in only a few residues, are equivalent to the carA gene of the present invention.

The DNA sequence past, or downstream of, the termination codon of the carA coding sequence comprises a transcription terminator. Transcription terminators can impart stability upon transcripts and play a regulatory role. Restriction fragments containing the transcription termination sequence of the carA gene can be conveniently isolated from *Streptomyces thermotolerans* DNA and used to prepare recombinant genes for expression in Streptomyces.

Although many of the above-described vectors comprise the Streptomyces replicon derived from plasmid pIJ702, a variety of known Streptomyces replicons can be used to construct equally useful vectors with different host ranges. Table X is an illustrative, but not comprehensive, listing of Streptomyces plasmids from which Streptomyces replicons can be obtained. Those skilled in the art recognize that, so long as the replicon function is not disrupted, all or part of the plasmids can be used to construct vectors that contain the carA gene of the present invention. The plasmid-containing host and depository accession number are also listed in Table X.

TABLE X
Streptomyces Plasmids

| Plasmid | Host | Accession Number |
|---|---|---|
| SCP2 | Streptomyces coelicolor A3(2) | NRRL 15042 |
| SCP2* | Streptomyces coelicolor M110 | NRRL 15041 |
| pEL7 | Streptomyces ambofaciens/pEL7 | NRRL 12523 |
| pUC6 | Streptomyces espinosus | NRRL 11439 |
| pUC3 | Streptomyces 3022A | NRRL 11441 |
| SLP1 | Streptomyces lividans | NCIB* 11417 |
| pNM100 | Streptomyces virginiae | NRRL 15156 |
| pEL103 | Streptomyces granuloruber A399 12.13/pEL103 | NRRL 12549 |
| pIJ702 | Streptomyces lividans | ATCC** 39155 |

*National Collection of Industrial Bacteria (NCIB), Torry Research Station, Post Office Box 31, 135 Abbey Road, Aberdeen AB98DG, Scotland, United Kingdom.
**American Type Culture Collection, Rockville, MD 20852.

Restriction fragments used to construct vectors illustrative of the present invention can be conventionally modified to facilitate ligation. For example, molecular linkers can be provided to a particular carbomycin resistance gene-containing restriction fragment or to DNA comprising vector replication or integration functions. Thus, specific sites for subsequent ligation can be conveniently constructed. In addition, the various carbomycin resistance gene-containing restriction fragments, origin of replication, or sequences that provide for chromosomal integration of a given vector can be modified by adding, eliminating, or substituting certain nucleotides to alter characteristics and to provide a variety of restriction sites for ligation of DNA. Those skilled in the art understand nucleotide chemistry and the genetic code and thus which nucleotides are interchangeable and which DNA modifications are desirable for a specific purpose. It is also noteworthy that given carbomycin resistance gene-containing restriction fragment is not limited to a particular position on a cloning vector, as long as critical, vector-controlled functions are not disrupted. Those skilled in the art understand or can readily determine which sites on a vector are advantageous for the ligation or insertion of a particular carbomycin resistance gene-containing restriction fragment.

Of course, the carA gene can be used to construct vectors other than plasmids. Phage φC31 is a well-known Streptomyces phage that is an excellent source of starting material for constructing integrative carbomycin resistance-conferring vectors that further exemplify the present invention. A derivative of phage φC31, phasmid pKC331, is especially preferred for constructing such integrating vectors and can be obtained from E. coli K12 BE447/pKC331 (NRRL B-15828). φC31-type phages are integrative vectors and can be readily modified to incorporate the carA gene and thus confer carbomycin resistance to Streptomyces.

The vectors of the present invention comprise a Streptomyces replicon and a carbomycin resistance-conferring restriction fragment. Because amplification and manipulation of plasmids is done faster and more efficiently in E. coli than in Streptomyces, it is convenient to add DNA sequences that also allow for replication in E. coli. Thus, the addition of functional replicon-containing and antibiotic resistance-conferring restriction fragments from E. coli plasmids such as, for example, pBR322, pACYC184, pBR325, pBR328, and the like is highly advantageous and adds to the general utility of the present illustrative vectors.

The carA gene confers resistance to carbomycin and other antibiotics. In Streptomyces griseofuscus, the carA confers resistance to carbomycin, spiramycin, and lincomycin. In S. lividans, carA increases resistance to erythromycin and oleanodomycin. Inducible resistance to macrolide antibiotics, such as carbomycin and erythromycin, in Gram-positive bacteria (such as Staphylococcus, Streptomyces, Streptococcus, and Bacillus) is associated with co-resistance to lincosamide and streptogramin-type B antibiotics; this multi-drug-resistant phenotype is called the MLS-resistant phenotype (Fujisawa and Weisblum, 1981, J. Bacteriol. 146:621–631).

The carA gene confers a modified MLS-resistant phenotype. Table XI, below, presents the results of disc-sensitivity assays, which demonstrate that the carA gene confers resistance to a number of antibiotics. The carA-containing cells were cultured in 0.1 μg/ml carbomycin prior to the assays.

The carA gene can confer resistance to a greater variety of MLS antibiotics when cells containing the carA gene are cultured under inducing conditions prior to selection with antibiotic, i.e., induction with erythromycin or oleandomycin in S. griseofuscus cells containing the carA gene makes the cells resistant to tylosin. Inducing conditions are achieved by exposing the cells to subinhibitory concentrations of certain macrolide antibiotics and other antibiotics that bind to the 50S subunit of the ribosomes. Different species of Streptomyces will exhibit different induction patterns.

TABLE XI
Antibiotic Resistance Pattern

| | | S. griseofuscus | |
|---|---|---|---|
| Antibiotic[a] | S. thermotolerans | pIJ702 | pOJ158 |
| erythromycin | 23 | R[b] | R |
| oleandomycin | 15 | R | R |
| carbomycin | R | 26 | R |
| spiramycin | R | 20 | R |
| tylosin | 16 | 24 | 17 |
| rosamycin | R[b] | 37 | 15 |
| lincomycin | R | 13 | R[b] |
| vernamycin B | R[b] | 16 | 11[c] |

[a]20 μg of antibiotic per disc; numbers refer to zone diameters; R indicates no zone
[b]small zone of growth inhibition.
[c]turbid zone.

The relatively large zones of inhibition of growth around the discs show that Streptomyces griseofuscus/pIJ702 is quite sensitive to MLS antibiotics, except for erythromycin and oleandomycin. In the presence of pOJ158, the zone sizes are considerably smaller or absent, because of increased resistance to these antibiotics as a result of expression of the carA gene. Vernamycin B gave a turbid zone that is due to inducible or partial resistance to vernamycin B. The small, but clearly discernable zones around the lincomycin disc shows that this antibiotic causes inhibition of growth at lower concentrations than do the other antibiotics tested. The minimal concentration of carbomycin that inhibits growth is given in Table XII, below. Resistance to erythromycin and oleandomycin was analyzed in S. lividans, because this strain is sensitive to these antibiotics. S. lividans transformants containing the carA gene are more resistant to erythromycin and oleandomycin even though S. thermotolerans is sensitive to these antibiotics.

As can be seen from Tables XI and XII, the level of macrolide antibiotic required to observe growth inhibition of a sensitive strain varies and depends on the particular antibiotic, host strain, and growth conditions. Those skilled in the art will recognize that the precise experimental conditions, including the preferred macrolide antibiotic concentration, for using the carA gene for purposes of selection can be readily determined by empirical methods. A preferred procedure for determining an organism's sensitivity to carbomycin utilizes antibiotic-gradient plates, as exemplified in Table XII, to measure the minimum inhibitory concentration (MIC) of antibiotic needed to inhibit cell growth. Disc-sensitivity assays can also be used to determine an organism's sensitivity to carbomycin, as exemplified in Table XI. The vectors of the present invention can increase the endogenous resistance to carbomycin by about 100 fold. Variations in this increase are expected when different promoters are used to drive expression of the carA gene.

TABLE XII

| Strain | MIC (μg/ml) carbomycin[a] |
| --- | --- |
| S. griseofuscus | 0.5 |
| S. griseofuscus/pIJ702 | 0.5 |
| S. griseofuscus/pOJ158 | 30 |
| S. thermotolerans | >1000 |

[a]values were determined on antibiotic gradient plates (Szybalski, 1952, Science 116:46–48)

*Streptomyces thermotolerans* contains two carbomycin resistance-conferring genes, designated carA and carB. The level of carbomycin resistance in the *S. griseofuscus* transformants was lower than in *S. thermotolerans*, because the two carbomycin resistance genes act in concert to cause high-level resistance in the antibiotic-producing organism. Alternatively, carA may not be expressed as efficiently in *S. griseofuscus* as in *S. thermotolerans*. The carB gene is disclosed and claimed in, Epp et al., U.S. patent application Ser. No. 06/901,334, filed herewith at even date. The present invention comprises vectors that encode both the carA and carB genes.

The recombinant DNA cloning vectors of the present invention have broad utility and help fill the need for suitable cloning vehicles for use in Streptomyces and related organisms. Moreover, the ability of the present vectors to confer carbomycin resistance provides a functional means for selecting transformants. This is important because of the practical necessity for determining and selecting the particular cells that have acquired vector DNA in a transformation procedure.

Additional DNA segments, that lack functional tests for their presence, can also be inserted into the present vectors, and transformants containing the non-selectable DNA can be isolated by selection for carbomycin resistance. Such non-selectable DNA segments can be inserted at any site, except within regions necessary for plasmid function and replication or within the carA gene, and include, but are not limited to, genes that specify antibiotic modification enzymes and regulatory genes of all types.

More particularly, a non-selectable DNA segment that comprises a gene is inserted into a plasmid such as, for example, plasmid pOJ158 at the central ClaI restriction site of the thiostrepton resistance gene. Such an insertion inactivates the thiostrepton resistance gene and thus allows for the easy identification of transformants containing the recombinant plasmid. This is done by first selecting for carbomycin resistance and, secondarily, identifying those carbomycin-resistant transformants that are not resistant to thiostrepton. Therefore the ability to select for carbomycin resistance in Streptomyces and related cells allows for the efficient isolation of the relatively few cells that contain the particular non-selectable DNA of interest.

The functional test for carbomycin resistance, described above, is also used to locate DNA segments that act as control elements and direct expression of an individual antibiotic resistance-conferring gene. Such segments, including, but not limited to, promoters, attenuators, repressors, inducers, ribosome-binding sites, and the like, are used to control the expression of other genes in Streptomyces and related organisms.

The carbomycin resistance-conferring vectors of the present invention are also useful for ensuring that linked DNA segments are stably maintained in host cells over many generations. These genes or DNA fragments covalently linked to the carbomycin resistance-conferring DNA and propagated in Streptomyces, are maintained by exposing the transformants to levels of carbomycin toxic to non-transformed cells. Therefore, transformants that lose the vector, and consequently lose any covalently linked DNA, cannot grow and are eliminated from the culture. Thus, the vectors of the present invention can stabilize and maintain DNA sequences of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Tobramycin, Erythromycin, and the like. The present invention also provides selectable vectors that are useful for cloning, characterizing, and reconstructing DNA sequences that code for: commercially important proteins such as, for example, human insulin, human proinsulin, glucagon, interferon and the like; enzymatic functions in metabolic pathways leading to commercially important processes and compounds; or control elements that improve gene expression. These desired DNA sequences also include, but are not limited to DNA that codes for enzymes that catalyze synthesis of derivatized antibiotics such as, for example, Streptomycin, Cephalosporin, Tylosin, Actaplanin, Narasin, Monensin and Erythromycin derivatives, or for enzymes that mediate and increase bioproduction of antibiotics or other products. The capability for isolating and using such DNA segments allows for increasing the yield and availability of antibiotics that are produced by Streptomyces and related organisms.

Streptomyces can be cultured in a number of ways using any of several different media. Preferred carbohydrate sources in a culture medium include, for example, molasses, glucose, dextrin, and glycerol. Nitrogen sources include, for example, soy flour, amino acid mixtures, and peptones. Nutrient inorganic salts are also incorporated and include the customary salts capable of yielding sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

Streptomyces is grown under aerobic culture conditions over a relatively wide pH range of about 5 to 9 a temperatures ranging from about 15° to 40° C. For plasmid stability and maintenance, it is desirable to start with a culture medium at a pH of about 7.2 and maintain a culture temperature of about 30° C.

The following examples further illustrate and describe the invention disclosed herein. The invention is not limited in scope by reason of any of the following Examples; sources of reagents or equipment are provided merely for convenience and in no way limit the invention. Both an explanation of and the actual procedures for constructing the invention are described where appropriate.

EXAMPLE 1

Isolation of Plasmid pOJ158

A. Culture of *Streptomyces griseofuscus* C581/pOJ158

About $10^8$ spores of *Streptomyces griseofuscus* C581/pOJ158 (NRRL 18089) are inoculated into 10 ml of TSB medium (Trypticase Soy Broth*) containing 25 μg/ml thiostrepton and grown at 29° C. until the culture is in early stationary phase. The culture was then homogenized, and 5 ml of the homogenized culture were used to inoculate 100 ml of TSB also containing thiostrepton. The 100 ml of culture were incubated at 29° C. until the *Streptomyces griseofuscus* C581/pOJ158 cells reached stationary phase.

TSB is made at 30 g/l and is obtained from Baltimore Biological Laboratories (BBL), P.O. Box 243, Cockeysville, Md. 21031.

B. Plasmid Isolation

The cells were collected and washed once with a 10.3% sucrose solution. The cells were then suspended in 24 ml of 10.3% sucrose, and 6 ml of 5X lysozyme solution (125 mM Tris-HCl, pH=8; 125 mM Na$_2$EDTA, pH=8; 10 mg/ml lysozyme; and 10.3% sucrose) were added. The solution was mixed and then incubated at 30° C. for 30-60 minutes, and then, about 18 ml of a solution that was 0.3M NaOH, 1% SDS, and prewarmed to 50° C. were added, mixed and the resulting mixture incubated at 80° C. for 10 minutes. The mixture was then cooled to room temperature, and 12 ml of a solution made by mixing 500 g phenol and 500 g CHCl$_3$ in 200 ml H$_2$O were added and mixed well with the cell-extract. The phases were separated by centrifugation at 6000-8000 rpm for 10 minutes; approximately 45 ml of the resulting upper phase were transferred to a clean bottle.

Next, 4.5 ml of 3M sodium acetate (NaOAc) and 50 ml of isopropanol were added to the supernatant, and the solution was mixed and left at room temperature for 30 minutes. The solution was then centrifuged (8000 rpm for 30 minutes) and the resulting supernatant discarded. The pellet was resuspended in 10 ml of TE buffer (10 mM Tris-HCl, pH=8, and 1 mM EDTA) containing 9.5 g of CsCl. About 1 ml of a 5 mg/ml solution of ethidium bromide was added to the solution to bring the final volume to 12.5 ml. The solution was then centrifuged at 52,000 rpm for 48 hours at 20° C. in a Beckman Ti-75 fixed-angle rotor. The fraction containing the plasmid band was extracted 5 times with isopropanol saturated with 20X SSC (0.3M NaCl and 0.3M NaCitrate) to remove the ethidium bromide. After the extractions, the sample was dialyzed against 1000 volumes of H$_2$O and then against 1500 volumes of TE buffer. The procedure yields about 100 μg of plasmid pOJ158 DNA at a concentration of ~0.2 μg/μl and is stored at 4° C. A restriction site and function map of plasmid pOJ158 is presented in FIG. 1 of the accompanying drawings.

EXAMPLE 2

Construction of Plasmid pOJ197

A. Isolation of Plasmid pOJ160

Plasmid pOJ160 can be obtained from the Northern Regional Research Center in *E. coli* K12 JM109 under the accession number NRRL B-18088. The lyophils of *E. coli* K12 JM109/pOJ160 are plated onto L-agar plates (10 g of Bacto-tryptone, 10 g of NaCl, 5 g of Bacto-Yeast Extract, and 15 g of agar per liter) containing 200 μg/ml apramycin to obtain a single colony isolate of the strain. This colony is used to inoculate about 500 ml of L broth (L agar without agar) containing 200 μg/ml apramycin, and the resulting culture is incubated at 37° C. with aeration until the cells reach stationary phase.

Plasmid DNA was obtained from the cells to use in construction of plasmid pOJ197 in accordance with the following procedure, which is adapted from Maniatis et al., 1982, *Molecular Cloning* (Cold Spring Harbor Laboratory). This same procedure was used, but on a smaller scale and with the ultracentrifugation steps replaced with phenol followed by chloroform extractions, to prepare the plasmid DNA used to identify the *E. coli* K12 RR1ΔM15/pOJ197 transformants.

About 500 ml of stationary-phase *E. coli*/pOJ160 cells are harvested by centrifugation at 4000Xg for 10 minutes at 4° C., and the supernatant is discarded. The cell pellet is washed in 100 ml of ice-cold STE buffer (0.1M NaCl; 10 mM Tris-HCl, pH 7.8; and 1 mM EDTA). After the cell pellet is washed, the pellet is resuspended in 10 ml of Solution 1 (50 mM glucose; 25 mM Tris-HCl, pH=8.0; and 10 mM EDTA) that contains 5 mg/ml lysozyme and is left at room temperature for 10 minutes. Twenty ml of Solution 2 (0.2N NaOH and 1% SDS) are then added to the lysozyme-treated cells, and the solution is gently mixed by inversion. The mixture is incubated on ice for 10 minutes.

Fifteen ml of ice-cold, 3M sodium acetate, pH=4.8, are added to the lysed-cell mixture, and the solution is mixed by inversion. The solution is incubated on ice for 60 minutes. The 3M sodium acetate solution is prepared by mixing equal volumes of 3M acetic acid and 3M sodium acetate.

The lysed cell mixture is centrifuged in a Beckman SW27 rotor (or its equivalent) at 20,000 rpm for 20 minutes at 4° C. About 36 ml of supernatant are recovered, and 2.5 volumes of ethanol are added, mixed, and the resulting solution left on ice for 15 minutes. The plasmid DNA is collected by centrifugation at 12,000Xg for 30 minutes at room temperature. The supernatant is discarded, and the DNA pellet is washed with 70% ethanol at room temperature. The ethanol wash is decanted, and the pellet is dried in a vacuum desiccator. The pellet is then resuspended in 8 ml of TE buffer.

Eight grams of CsCl are added to the DNA solution. About 0.8 ml of a 10 mg/ml solution of ethidium bromide in water are added for each 10 ml of CsCl-DNA solution. The final density of the solution is about 1.55 g/ml, and the ethidium bromide concentraton is about 800 μg/ml. The solution is transferred to a Beckman Type 50 centrifuge tube, filled to the top with TE buffer containing 1.55 g/ml CsCl, sealed, and centrifuged at 45,000 rpm for 24 hours at 20° C. After centrifugation, two bands of DNA are visible in ordinary light and become even more prominent in UV light. The cap is removed from the tube, and the lower DNA band is recovered using a syringe with a #21 hypodermic needle inserted through the side of the centrifuge tube.

The ethidium bromide is removed from the solution of plasmid DNA by several extractions with water-saturated 1-butanol, and the CsCl is removed by dialysis against TE buffer. After extractions with buffered phenol and then chloroform, the DNA is precipitated, washed with 70% ethanol, and dried. About 0.5 mg of plasmid pOJ160 DNA can be obtained by this procedure.

B. Final Construction of Plasmid pOJ197

About 1 μg (1 μl) of plasmid pOJ160 DNA was added to 2 μl of 10X PstI buffer (500 mM Tris-HCl, pH=7.5; 0.5M NaCl; and 100 mM MgCl$_2$), 16 μl of H$_2$O, and 1 μl (~15 units; unit definitions herein correspond to those of New England Biolabs, 32 Tozer Road, Beverly, Mass. 01915-9990, unless otherwise indicated) of restriction enzyme PstI. The resulting reaction was incubated at 37° C. for two hours. The reaction mixture was extracted with 100 μl of a 1:1 solution of phenol:chloroform and then with 100 μl of chloroform. The PstI-digested DNA was collected by adjusting the sodium acetate (NaOAc) concentration of the reaction mixture to 0.30M, adding 2.5 volumes of ethanol, chilling the reaction mixture to −70° C., and centrifuging to pellet the precipitated DNA. The pellet of PstI-digested plasmid pOJ160 DNA was resuspended in 1 μl of 10X EcoRI buffer (1.0M Tris-HCl, pH=7.5; 0.5M NaCl; 50 mM MgCl$_2$; and 1 mg/ml BSA), 18 μl of H$_2$O, and 1 μl (~20 units) of restriction enzyme EcoRI. The resulting reaction was incubated at 37° C. for 2 hours; then, the reaction mixture was extracted and the DNA collected as described above. The EcoRI-PstI-digested plasmid pOJ160 DNA was resuspended in 1 μl of H$_2$O.

About 10 μg of plasmid pOJ158 in 100 μl of TE buffer were added to 13 μl of 10X PstI buffer, 13 μl of H$_2$O and 4 μl (~60 units) of restriction enzyme PstI. The resulting reaction was incubated at 37° C. for 2 hours. The reaction mixture was extracted and the DNA collected as described above; then, the PstI-digested plasmid pOJ158 DNA was resuspended in 10 μl of 10X EcoRI buffer, 3 μl (~60 units) of restriction enzyme EcoRI, and 87 μl of H$_2$O. The reaction was incubated at 37° C. for 2 hours.

The PstI-EcoRI-digested plasmid pOJ158 DNA was then electrophoresed on a 1% agarose gel until the desired ~4 kb PstI-EcoRI restriction fragment was clearly separated from the other digestion products. Visualization of the electrophoresed DNA was accomplished by staining the gel in a dilute solution (0.5 μg/ml) of ethidium bromide and exposing the stained gel to longwave UV light. After the desired fragment was located, a small slit was made in the gel in front of the fragment, and a small piece of Schleicher and Schuell (Keene, N.H. 03431) NA-45 DEAE membrane was placed in the slit. Upon further electrophoresis, the ~4 kb PstI-EcoRI restriction fragment was non-covalently bound to the DEAE membrane. After the desired fragment was bound to the DEAE membrane, the membrane was removed and rinsed with low salt buffer (150 mM NaCl; 0.1 mM EDTA; and 20 mM Tris-HCl, pH=8). Next, the membrane was placed in a small tube and immersed in high salt buffer (1 M NaCl; 0.1 mM EDTA; and 20 mM Tris-HCl, pH=8) and then incubated at 65° C. for one hour to elute the DNA from the DEAE paper. After the 65° C. incubation, the incubation buffer was collected and the membrane rinsed with high salt buffer. The rinse solution was pooled with the incubation buffer before collecting the desired DNA fragments.

About three volumes of cold, absolute ethanol were added to the high salt-DNA solution. The resulting solution was mixed and placed on ice for 10-20 minutes and then centrifuged at 15,000 rpm for 15 minutes. After another precipitation to remove residual salt, the DNA pellet was rinsed with ethanol, dried, resuspended in 50 μl of TE buffer, and constituted ~2.5 μg of the desired ~4 kb PstI-EcoRI restriction fragment of plasmid pOJ158.

The PstI-EcoRI-digested plasmid pOJ160 DNA (1 μl) was added to 10 μl (~0.5 μg) of the ~4 kb, carA-containing PstI-EcoRI restriction fragment of plasmid pOJ158, 2 μof 10X ligase buffer (660 mM Tris-HCl, pH=8; 66 mM MgCl$_2$; 10 mM dithiothreitol (DTT); and 10 mM ATP), and 6 μl of H$_2$O. About 1 μl (~100 units) of T4 DNA ligase was added to the solution of DNA, and the resulting reaction was incubated at 15° C. overnight (~16 hours). The ligated DNA constituted the desired plasmid pOJ197; a restriction site and function map of plasmid pOJ197 is presented in FIG. 2 of the accompanying drawings.

The EcoRI and PstI sites on plasmid pOJ160 reside within a polylinker that itself forms part of the DNA sequence encoding the lacZ α-fragment. Expression of the lacZ α-fragment in an *E. coli* ΔM15 strain, such as *E. coli* K12 RR1ΔM15 (NRRL B-15440), restores the strain's ability to produce a functional β-galactosidase enzyme. Thus, plasmid pOJ160 can restore β-galactosidase activity to the *E. coli* K12 RR1ΔM15 strain. However, insertion of DNA into a restriction site of the polylinker on plasmid OJ160, as occurs in the construction of plasmid pOJ197, disrupts the lacZ α-fragment coding sequence and concomitantly destroys the ability of the plasmid pOJ160 derivative to complement the ΔM15 mutation. β-galactosidase can hydrolyze X-Gal, which is 5-bromo-4-chloro-3-indolyl-β-D-galactopyranoside, a colorless compound, to an indigo-colored product and thus allows for a convenient screening method for discriminating between transformants containing starting plasmid pOJ160 and those containing a plasmid pOJ160 derivative, such as plasmid pOJ197.

To prepare *E. coli* K12 RR1ΔM15 cells that are competent for transformation, the lyophils of *E. coli* K12 RR1ΔM15 obtained from the NRRL are reconstituted to isolate single colonies. One single-colony isolate of RR1ΔM15 is inoculated into 5 ml of L broth (10 g of Bacto-tryptone, 10 g of NaCl, and 5 g of Bacto-Yeast Extract per liter) that contains 10 mM MgSO$_4$ and 10 mM MgCl$_2$, and the culture is incubated at 37° C. overnight with aeration. Fifty μl of the overnight culture are used to inoculate 5 ml of L broth that contains 10 mM MgSO$_4$ and 10 mM MgCl$_2$. The culture is incubated at 37° C. overnight with aeration. The following morning, the culture is diluted to 200 ml with L broth that contains 10 mM MgSO$_4$ and 10 mM MgCl$_2$. The diluted culture is incubated at 37° C. with aeration until the absorbance at 550 nm (A$_{550}$) is about 0.5, which indicates a cell density of about $1 \times 10^8$ cells/ml. The culture is cooled for ten minutes in an ice-water bath, and the cells are then collected by centrifugation at 4000Xg for 10 minutes at 4° C. The cell pellet is resuspended in 100 ml of cold 10 mM NaCl and then immediately repelleted by centrifugation. The cell pellet is resuspended in 100 ml of 30 mM CaCl₂ and incubated on ice for 20 minutes.

The cells are again collected by centrifugation and resuspended in 10 ml of 30 mM CaCl₂. A one-half ml aliquot of the cells was added to the ligated DNA prepared above. The cell-DNA mixture was incubated on ice for one hour, heat-shocked at 42° C. for 90 seconds, and then chilled on ice for about two minutes. The cell-DNA mixture was centrifuged, and the cell pellet was resuspended into 0.5 ml of L broth in a 1.5 ml tube and incubated at 37° C. for one hour.

Aliquots of the transformation mixture were plated on L-agar (L-broth with 15 grams per liter agar) plates containing 200 μg apramycin/ml, 40 μg X-gal/ml, and 40 μg IPTG/ml. IPTG serves to derepress the lac promoter present on plasmid pOJ160. The plates were incubated at 37° C. overnight. Colonies that contain a plasmid without an insert, such as *E. coli* K12 RR1ΔM15/pOJ160, appear blue on these plates. Colonies that contain a plasmid with an insert, such as *E. coli* K12 RR1ΔM15/pOJ197, are white. Several apramycinresistant, white colonies were selected and then screened by restriction enzyme analysis of their plasmid DNA for the presence of the ~4 kb EcoRI-PstI restriction fragment. Plasmid DNA was obtained from the *E. coli* K12 RR1ΔM15/pOJ197 transformants in accordance with the procedure for isolating plasmid pOJ160 DNA, described above. The plasmid pOJ197 DNA can be used to transform *Streptomyces lividans* TK23 and *Streptomyces griseofuscus* C581 to carbomycin resistance, as described in Example 3, below.

EXAMPLE 3

Construction of Carbomycin-Resistant *Streptomyces lividans* TK23 and *S. griseofuscus* C581

A. List of Solutions

The following solutions are referred to throughout the Examples and are presented here for clarity.

1. P medium (~100 ml):

| Ingredient | Amount |
| --- | --- |
| Sucrose | 10.3 g |
| K₂SO₄ | 0.025 g |
| Trace element solution (see #3) | 0.2 ml |
| MgCl₂.6H₂O | 0.203 g |
| Water | 80 ml |
| After autoclaving add: | |
| KH₂PO₄ (0.5%) | 1 ml |
| CaCl₂.2H₂O (3.68%) | 10 ml |
| (N—tris-(hydroxymethyl)-methyl-2-aminoethane sulphonic acid), "TES" buffer, 0.25 M, pH = 7.2 | 10 ml |

2. Trace element solution (~1 L):

| Ingredient | Amount |
| --- | --- |
| ZnCl₂ | 40 mg |
| FeCl₃.6H₂O | 200 mg |
| CuCl₂.2H₂O | 10 mg |
| MnCl₂.4H₂O | 10 mg |
| Na₂B₄O₇.10H₂O | 10 mg |
| (NH₄)₆Mo₇O₂₄.4H₂O | 10 mg |
| H₂O | 1 L |

3. R2 Regeneration Medium (~1 L):

| Ingredient | Amount |
| --- | --- |
| Sucrose | 103 g |
| K₂SO₄ | 0.25 g |
| Trace element solution | 2 ml |
| MgCl₂.6H₂O | 10.12 g |
| glucose | 10 g |
| L-asparagine.1H₂O | 2.0 g |
| casamino acids | 0.1 g |
| Agar | 22 g |
| Water | to 700 ml |
| The pH is adjusted to pH = 7.2 before autoclaving. After autoclaving, add: | |
| KH₂PO₄ (0.05 g/100 ml) | 100 ml |
| CaCl₂ (2.22 g/100 ml) | 100 ml |
| TES Buffer (5.73 g/100 ml, pH = 7.2) | 100 ml |

4. Soft nutrient agar (SNA, ~1 L):

| Ingredient | Amount |
| --- | --- |
| Difco Bacto Nutrient Broth | 8 g |
| Agar | 5 g |

5. R2YE medium is R2 medium with 20 ml of 25% yeast extract added per liter.

6. Yeast Extract—Malt Extract (YEME, ~1 L):

| Ingredient | Amount |
| --- | --- |
| Yeast extract | 3 g |
| Peptone | 5 g |
| Malt extract | 3 g |
| Glucose | 10 g |

7. YEME+34% Sucrose Liquid Complete Medium is YEME with 340 g/L of sucrose.

8. YMX Media (~1 L):

| Ingredient | Amount |
| --- | --- |
| Yeast extract | 3 g |
| Malt extract | 3 g |
| Glucose | 2 g |
| Agar | 20 g |

9. YMX Agar is 0.3% yeast extract, 0.3% malt extract, 0.2% dextrose, and 2.0% agar.

B. Transformation of *Streptomyces griseofuscus*

Plasmid pOJ158 was first isolated by transforming a library of MboI-digested *Streptomyces thermotolerans* (ATCC 11416) DNA cloned into BglII-digested plasmid pIJ702 DNA into *S. griseofuscus* C581 (ATCC 23916). A number of thiostrepton-resistant transformants were isolated, homogenized, grown in media containing 0.5 μg/ml carbomycin for about 16 hours, and, finally, plated on media containing 10 μg/ml carbomycin. The transforming DNA was prepared from the carbomycinresistant transformants in substantial accordance with the procedure of Example 1. A similar procedure was used with the ligated DNA prepared in Example 2 to obtain *S. griseofuscus* C581/pOJ197 transformants.

*Streptomyces griseofuscus* C581 (ATCC 23916) was plated on YMX agar and incubated at 30° C. for about 72 hours. A plug of cells was removed from the plate and used to inoculate 10 ml of TSB. The culture was homogenized and incubated at 30° C. for ~30 hours. About 4 ml of this culture were homogenized and used to inoculate 100 ml of TSB containing 0.4% glycine. The culture was incubated at 30° C. for about ~24 hours. About 4 ml of this culture were again homogenized and used to inoculate 100 ml of TSB containing 0.4% glycine. The culture was incubated at 30° C. for about 16 hours. The cells were harvested and washed three times with 10.3% sucrose. The cells were resuspended in 100 ml of P media containing 1 mg/ml lysozyme, and the resulting solution was incubated at 30° C. for 2 hours. During this protoplasting step, the cells were pipetted up and down to disperse clumps. The protoplasts were collected and washed three times with P medium. The protoplasts were then suspended in 10 ml of P medium. This process usually generates about 2 to $5 \times 10^7$ protoplasts per 150 $\mu$l of solution.

Approximately 150 $\mu$l of the protoplast solution were added to 10 $\mu$l of the transforming DNA, either in ligation or TE buffer, and mixed. About 101 $\mu$l of 50% polyethylene glycol 1000 in P media were then added and mixed. After a brief (1 to 2 minutes) incubation at room temperature, the cell-DNA mixture was brought to a volume of 1 ml by the addition of P media. The cell suspension was plated onto R2 medium; about 0.1 ml of cells was inoculated per R2 plate. The plates were incubated at 30° C. overnight (~16 hours) and then overlaid with ~3 ml of R2-modified agar (103 g sucrose, 10.12 g MgCl$_2$, 2.22 g CaCl$_2$, and 5.72 g TES at pH=7.2 per liter) containing enough thiostrepton to give a final concentration, after diffusion, of 25 $\mu$g/ml. The plates were then incubated for about four days at 30° C., when colonies became visible to the naked eye.

Carbomycin-resistant transformants were selected by patching regenerated protoplasts to R2 medium containing 10 $\mu$g/ml of carbomycin. Alternatively, carbomycin-resistant transformants were selected by inoculating the regenerated protoplasts into TSB containing 0.5 $\mu$g/ml carbomycin. The culture was incubated for 16–22 hours at 30° C. before plating the cells onto media containing 10 $\mu$g/ml carbomycin. As plasmids pOJ158 and pOJ197 also comprise a thiostrepton resistance-conferring gene, thiostrepton, at a final concentration of 20 $\mu$g/ml, was also used to select transformants.

The transformants were cultured on R2 agar supplemented with carbomycin (10 $\mu$g/ml) to obtain single colonies. These single colonies were used to inoculate 10 ml TSB cultures containing both carbomycin and thiostrepton (25 $\mu$g/ml). The cultures were homogenized and then grown overnight at 30° C. in a rotary shaker.

Plasmid isolation for analysis was done by a small-scale version of the protocol of Example 1; the CsCl gradients of Example 1 were replaced by ethanol precipitations. The mycelium was collected by centrifugation, washed twice with 10.3% sucrose and then suspended in 1–2 ml of 10.3% sucrose. Four hundred $\mu$l of the cell mixture were transferred to a small tube, and 100 $\mu$l of 5X Lysozyme solution (Example 1) were added. The suspension was incubated at 30° C. for 30–60 minutes, followed by the addition and mixing of 300 $\mu$l of 0.3 M NaOH containing 1% SDS. The latter solution was kept at 50° C. before its addition to the cell mix. The cell mixture was placed at 80° C. for 10 minutes, cooled to room temperature, and then extracted with 200 $\mu$l of phenol:CHCl$_3$ (50:50). The aqueous phase was transferred to a clean tube, made 0.3 M in NaOAc, and then, one volume of isopropanol was added. The DNA was incubated at room temperature for five minutes and then pelleted by centrifugation. The pellet was dissolved in 500 $\mu$l of TE buffer, and about 25 $\mu$l of 0.1 M spermine were added to the solution of DNA, and the mixture was incubated at room temperature for 5 minutes. After centrifugation, the DNA pellet was rinsed with 75% ethanol, then resuspended and reprecipitated from 0.3 M sodium acetate using ethanol. After this last precipitation, the plasmid DNA was suspended in 50 $\mu$l of TE buffer. Restriction enzyme cutting and electrophoretic analysis of the reaction products were used to determine plasmid structure.

C. Preparation of *Streptomyces lividans* Protoplasts and Transformation to Carbomycin Resistance

*Streptomyces lividans* TK23 (NRRL 15826) was plated on R2 agar, and the plates were incubated at 30° C. for 16 hours. A plug of cells was taken from the plate and used to inoculate 10 ml of TSS-glycine (12% sucrose and 0.5% glycine in TSB). This culture was incubated at 30° C. for ~65 hours with aeration. The culture was then homogenized, sonicated, pelleted with centrifugation, and washed with 10 ml of P media. The cell pellet was resuspended in P media containing 2 mg/ml lysozyme, incubated at 4° C. for 15 minutes, mixed by inversion, and then incubated at 4° C. for 30 minutes. The resulting protoplasts were washed twice in P media and then resuspended in 10 ml of P media. For each sample of transforming DNA (~5 $\mu$l), 200 $\mu$l of protoplasts were added to the DNA, and then, 0.5 ml of 20% polyethylene glycol 1000 in P media was added to the cell-DNA mixture. The cells were then plated in 200 $\mu$l aliquots using ~3 ml of R2-modified overlays (103 g sucrose, 10.12 g MgCl$_2$, 2.22 g CaCl$_2$, and 5.73 g TES at pH =7.2 per liter). The plates were incubated at 30° C.

Thiostrepton and carbomycin were added and transformants identified as described for the preparation of *Streptomyces griseofuscus* transformants. *Streptomyces lividans* TK23 transformants containing the carA gene were prepared in accordance with the preceding procedure.

We claim:

1. A method for selecting a recombinant DNA-containing host cell that comprises transforming a carbomycin-sensitive actinomycetes host cell with a recombinant DNA vector that codes for the carA gene product and culturing the transformed cell under conditions suitable for selection of carbomycin-resistant transformants.

2. The method of claim 1 wherein said host cell is Streptomyces.

3. The method of claim 2 wherein said host cell is *Streptomyces griseofuscus*.

4. The method of claim 2 wherein said host cell is *Streptomyces lividans*.

5. A recombinant DNA that encodes the carA gene product of the method of claim 1.

6. The DNA of claim 5 that comprises the carA gene of *Streptomyces thermotolerans*.

7. A recombinant DNA vector that comprises the DNA of claim 5.

8. The vector of claim 7 that is a plasmid.
9. The plasmid of claim 8 that is plasmid pOJ158.
10. The plasmid of claim 8 that is plasmid pOJ197.
11. A host cell transformed with a recombinant DNA vector of claim 7.
12. The host cell of claim 11 that is Streptomyces.
13. The host cell of claim 11 that is *Streptomyces lividans*.
14. The host cell of claim 11 that is *Streptomyces griseofuscus*.
15. The host cell of claim 13 that is *Streptomyces lividans*/pOJ158.
16. The host cell of claim 13 that is *Streptomyces lividans*/pOJ197.
17. The host cell of claim 14 that is *Streptomyces griseofuscus*/pOJ158.
18. The host cell of claim 14 that is *Streptomyces griseofuscus*/pOJ197.
19. Plasmid pOJ160.

* * * * *